United States Patent
Phanstiel, IV et al.

(10) Patent No.: US 7,972,807 B1
(45) Date of Patent: Jul. 5, 2011

(54) DIAGNOSTIC TESTS FOR INFLAMMATORY BOWEL DISEASES

(75) Inventors: Otto Phanstiel, IV, Oviedo, FL (US); Navneet Kaur, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 426 days.

(21) Appl. No.: 12/139,710

(22) Filed: Jun. 16, 2008

Related U.S. Application Data

(60) Provisional application No. 60/945,976, filed on Jun. 25, 2007.

(51) Int. Cl.
   *C12Q 1/02* (2006.01)
(52) U.S. Cl. .................................................. 435/29
(58) Field of Classification Search .................. None
   See application file for complete search history.

(56) References Cited

OTHER PUBLICATIONS

Villanueva et al. "Chromatography, flow injection analysis and electrophoresis in computer-assisted comparative biochemistry: its application and possibilities in clinical research", J of Chromatography, 1988, 440, 261-273.*

Obayashi et al. "Polyamine metabolism in colonic mucosa from patients with ulcerative colitis", The American Journal of Gastroenoterology, 1992, 87(6):736-740.*

Weiss et al. "Intracellular polyamine levels of intestinal epithelial cells in inflammatory bowel disease", Inflamm Bowel Dis., 2004, 10(5):529-535.*

Macfarlane et al. "Mucosal bacteria in ulcerative colitis", British Journal of Nutrition, 2005, 93, Suppl. 1:S67-S72.*

\* cited by examiner

*Primary Examiner* — Jon P Weber
*Assistant Examiner* — Bin Shen
(74) *Attorney, Agent, or Firm* — Allen, Dyer, Doppelt, Milbrath & Gilchrist, P.A.

(57) ABSTRACT

Disclosed are diagnostic tests helpful in indicating presence of an inflammatory bowel disease (IBD) in a human patient. In one embodiment, the test comprises obtaining a sample of mucosal tissue from the ileum or sigmoid colon of the patient; evaluating sample quality by testing for cadaverine and continuing the diagnostic test if the sample has no detectable cadaverine; testing the cadaverine negative sample for N-acetylated spermine; and correlating a detectable level of N-acetylated spermine in the sample with presence of IBD in the patient. Another, less invasive, method disclosed includes a diagnostic test comprising isolating mononuclear leukocytes from the patient's blood; testing the isolated mononuclear leukocytes for level of spermidine; and correlating a level of spermidine higher than that in mononuclear leukocytes of normal subjects as indicative of an inflammatory bowel disease in the patient.

5 Claims, 14 Drawing Sheets

DIAGNOSTIC TESTS FOR INFLAMMATORY BOWEL DISEASES

RELATED APPLICATION

This application claims priority from co-pending provisional application Ser. No. 60/945,976, which was filed on 25 Jun. 2007, and which is incorporated herein by reference in its entirety.

FIELD OF THE INVENTION

The present invention relates to the field of human diseases and, more particularly, to inflammatory bowel disease, including ulcerative colitis and Crohn's disease.

BACKGROUND OF THE INVENTION

Polyamines are ubiquitous aliphatic amines found in both prokaryotic and eukaryotic cells.[1] The native polyamines, shown as 1-3 in FIG. 1, are essential growth factors and exist mainly as polycations at physiological pH.[2] They are biosynthesized within cells and can also be imported into cells via the polyamine transporter (PAT).[3] The polyamines have many functions within cells including key roles in cell proliferation (cancer)[4] and in the immune response.[5]

The role of polyamines in cancer is well established. Certain cancer tissues are unable to synthesize enough polyamines to sustain their growth rate and rely on polyamine import processes to make up the difference.[5] Since polyamines are essential for cell growth, it is not surprising that high levels of polyamines are found in rapidly-dividing cells and cancerous tissues. Moreover, the metabolites of polyamines are often found in the urine of cancer patients at higher levels than normal.[6] Indeed, $N^1,N^{12}$-diacetylspermine 9 (a byproduct of spermine) has been shown to be excellent tumor marker for colorectal cancer patients.[6-9]

Polyamines also play a role in the immune response.[5] Macrophages containing high levels of polyamines have significantly reduced phagocytotic ability.[10, 11] Indeed, spermine was recently shown to lower the immune response by inhibiting pro-inflammatory gene expression in macrophages activated by *H. pylori*.[5] Bussière et al have suggested that high spermine levels could prevent the antimicrobial effects of nitric oxide (NO) by inhibiting inducible nitric oxide synthase (iNOS) translation in activated macrophages.[5] To support this hypothesis, macrophage bacteriocidal activity was enhanced by transfection with a polyamine biosynthesis inhibitor (i.e., ornithine decarboxylase siRNA) and prevented by spermine addition.[5] These provocative results identified a "mechanism of immune dysregulation induced by the *H. pylori* bacterium in which stimulated spermine synthesis by the arginase-ODC pathway inhibits iNOS translation and NO production, leading to persistence of the bacterium and risk for peptic ulcer disease and gastric cancer."[5]

Inappropriate, dysregulated adaptive mucosal immune response to the intestinal bacteria (flora) is also a prerequisite for initiation and progression of the inflammatory process and tissue damage in inflammatory bowel diseases (IBD) like Crohn's disease (CD) and ulcerative colitis (UC). The mechanism of dysregulated adaptive immune response appears to be defective innate mucosal immunity. Abnormal mucosal macrophages are the key reason for defective innate immunity. For example, mutated recognition protein receptors (e.g. NOD-2, TLR-4) have been shown to be the cause of defective macrophage function in some of the CD patients.[12, 13] However, the mechanism of defective innate immunity in patients with UC has not been elucidated.

SUMMARY OF THE INVENTION

Our observations indicate that polyamine metabolism and transport is involved in ulcerative colitis (UC) progression (and possibly inflammatory bowel disease, IBD, in general). Indeed, the high polyamine content of inflamed IBD tissues may result in a reduced innate immune response by limiting the phagocytotic activity of circulating macrophages. A comparison between IBD and healthy tissues, revealed that the level of $N^1$-acetyl-spermine was significantly higher in IBD tissues and was not detected in the control healthy tissues. When the IBD tissues were segregated into clinically active and inactive categories, the IBD active tissues revealed increased levels of spermidine, spermine and $N^1$-acetyl-spermine. Indeed, the clinical activity tracked well with increased spermidine levels regardless of whether the tissue appeared inflamed or normal by endoscopy. Most important was the finding that active UC tissues gave statistically higher spermidine levels than either inactive UC tissue or the sigmoid control and that $N^1$-acetyl-spermine was detected in active UC tissues and not in the control samples. Crohns Disease (CD) samples were also investigated. Active CD gave higher spermidine and spermine levels than inactive CD tissues and the ileal control. However, the CD sigmoid results were equivocal except for the fact that $N^1$-acetyl-spermine was detected in the involved sigmoid but not in the control. In summary, the findings that both spermidine and $N^1$-acetyl-spermine are elevated in UC tissues suggest not only a potential new biomarker for UC (i.e., $N^1$-acetyl-spermine), but also identifies the role of polyamine metabolism in IBD progression for future study. Therefore, spermidine, spermine, $N^1$-acetyl-spermine and $N^1, N^{12}$-diacetylated spermine, all of which can be isolated from and detected in human bodily fluids, feces, urine and blood, are potentially useful indicators of IBD and even colon cancer.

Accordingly, and with the foregoing in mind, the present invention advantageously provides several diagnostic tests useful in sorting out the clinical presentation of patients with an unspecified inflammatory bowel disease (IBD). Some of these patients present with symptoms of IBD but, when examined by endoscopy, appear to have a normal intestinal mucosa. Therefore, in attempting to further focus the diagnosis, the clinician is in need of improved diagnostic tests, which are provided in the present invention.

In one preferred embodiment of the invention, a diagnostic test indicative of inflammatory bowel disease (IBD) in a human patient comprises first obtaining a sample of mucosal tissue from the ileum or sigmoid colon of the patient. The sample is evaluated for quality by testing for cadaverine and continuing the diagnostic test if the sample has no detectable cadaverine. As further explained below, presence of cadaverine in the tissue sample indicates that the sample would produce unreliable results in the diagnostic testing. Thus, cadaverine positive samples are unsuitable for testing according to the present invention. The method continues by testing the cadaverine negative sample for N-acetylated spermine and correlating a detectable level of N-acetylated spermine in the sample with presence of IBD in the patient. The clinician can, therefore, support an initial impression based on clinical symptoms with a laboratory diagnostic test wherein the positive sample is consistent with the IBD diagnosis.

Another embodiment of the invention provides a diagnostic test indicative of inflammatory bowel disease (IBD) in a symptomatic patient having an intestinal mucosa which appears normal by endoscopy. The test comprises obtaining a sample of mucosal tissue from the ileum or sigmoid colon of the patient and determining the sample has no detectable cadaverine before further testing. The cadaverine negative sample is tested for spermidine, spermine and $N^1$-acetylated spermine. Sample test results are compared to values for ileal or sigmoid mucosal tissue from normal subjects and higher than normal levels of spermine, spermidine and N-acetylated spermine are correlated as indicative of inflammatory bowel disease in the patient.

A variation of the method of the invention includes a diagnostic test indicative of inflammatory bowel disease in a patient having clinical symptoms consistent with said disease. This test comprises first obtaining a sample of intestinal mucosa from the patient. Before continuing the testing process, the method calls for ascertaining the sample has no detectable cadaverine. The cadaverine negative sample is then tested for spermidine and the sample's spermidine level is compared to level of spermidine in normal intestinal mucosal tissue. A higher than normal level of spermidine in the sample is correlated as indicative of inflammatory bowel disease in the patient.

Another preferred embodiment of the invention includes a diagnostic test for an inflammatory bowel disease in a patient symptomatic therefor. This method is less invasive in not requiring a tissue biopsy and comprises isolating mononuclear leukocytes from the patient's blood. The mononuclear cells are tested for level of spermidine and a level of spermidine higher than that in mononuclear leukocytes of normal subjects is correlated as indicative of an inflammatory bowel disease in the patient.

The invention also includes a diagnostic test useful in indicating where a patient may be afflicted with one of the more specific types of inflammatory bowel diseases, in particular, ulcerative colitis. Accordingly, in a patient symptomatic for an inflammatory bowel disease, the test comprises obtaining a sample of intestinal mucosa from the patient and, first, ascertaining the sample has no detectable cadaverine. Then, testing the cadaverine negative sample for levels of spermidine and N-acetylated spermine and comparing the sample's levels of spermidine and N-acetylated spermine to those in intestinal mucosa from normal subjects. Higher than normal levels of spermidine and N-acetylated spermine are indicative of ulcerative colitis in the patient.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 3 illustrates structures of N-dansylated polyamines and the N-acetylated metabolites, 1a-9a;

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

In this disclosure, $N^1$-acetylspermine, spermine, and spermidine have been identified as potential biomarkers for inflammatory bowel disease (IBD). Of these three, $N^1$-acetylspermine and spermidine were preferred as markers. In patients with active IBD the levels of these polyamines were significantly higher than control healthy tissues. In this regard, these compounds could be useful as medical diagnostic agents for determining the severity of IBD, its initial diagnosis, its current state of severity or its transition into colon cancer and its elevated levels represent a metabolic endpoint for colon cancer diagnosis.

Figure 2:
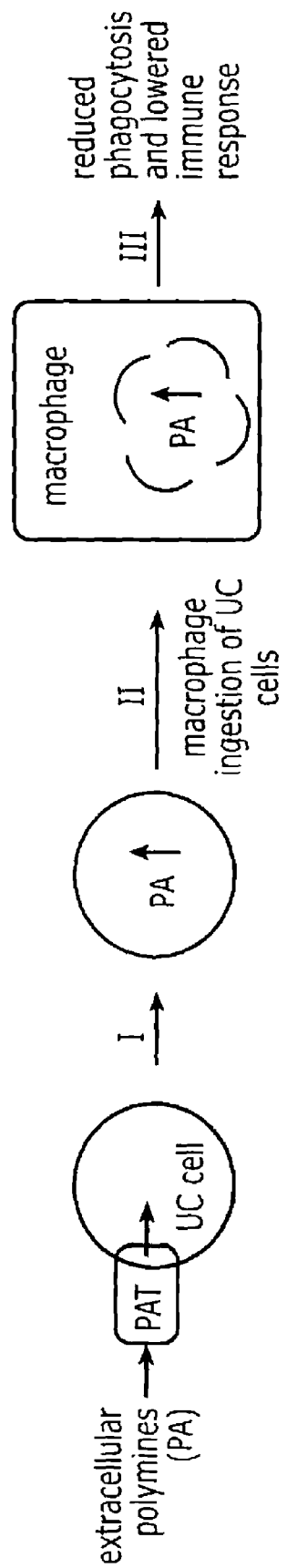
FIG. 2 depicts our hypothesis for UC disease progression and its relationship with polyamines, according to an embodiment of the present invention.

As shown in FIG. 2, our hypothesis in UC is that: i) high polyamine import activity may contribute to high intracellular polyamine content within UC cells, ii) ingestion of these cells by macrophages leads to high intra-macrophage polyamine concentrations, and iii) which would then result in a reduced immune response and disease progression via reduced macrophage phagocytosis activity[10, 11] and presumably reduced iNOS translation.[5]

A first step in support of this hypothesis is to demonstrate high polyamine content in IBD tissues. Thus, the aim of our study was to test this hypothesis by first determining whether the polyamine content in inflamed tissues of patients with IBD is abnormal. Forty nine tissue samples from both UC and CD patients and seven control samples were screened for polyamine content using a N-dansylation and HPLC protocol.[14] Significantly higher levels of spermidine (SPD), spermine (SPM) and $N^1$-acetylated spermine (NAcSPM, a spermine metabolite) were observed in patients with active inflammatory bowel disease (IBD). Further analyses were consistent with significantly higher levels of SPD in the sigmoid tissues from both active UC and Crohns as compared to inactive disease or healthy controls. In summary, spermidine levels are elevated in the sigmoid mucosa of active IBD patients.

Results and Discussion.

While both CD and UC are considered forms of IBD, their causes and disease progression are different. For example, one of the current hypotheses regarding CD etiology is that a luminal antigen may contribute to the disease state via adoptive immunity resulting in tissue damage. Indeed, defective innate immunity via NOD-2 and TLR mutations, have been shown to be relevant in CD but not in UC.[12, 13] In summary, although genetic susceptibility, immunodeficiency (innate and specific), nutrition and the enteric microfloral environment have been suggested as potential etiologies of CD,[15] the etiology of UC is unknown.

As mentioned above, the hypothesis relies on the presence of IBD tissues with high polyamine content. The purpose of this study was to survey both UC and CD tissues to see if there were statistically significant higher levels of polyamines in particular tissue types. In addition, we hoped to identify potential polyamine markers for these disease states.

Methods.

Typically, the patient biopsy tissues are homogenized and the polyamine contents are separated from the protein components. The protein content is measured by the Lowry method and provides the total mg of protein present. The polyamine fraction is then dansylated and extracted into an organic solvent, which is removed and replaced with acetonitrile and injected into an HPLC, which separates out the respective dansylated polyamine compounds. The area under the curve is converted to moles of polyamine using calibration curves generated from pure samples. Spermidine, spermine and $N^1$-acetylspermine are quantified as their dansylated derivatives in nmoles of compound. The final polyamine quantification is listed as nmol polyamine/mg protein.

Procedure for Extracting of Polyamines from Tissue Biopsies.

Saline (50 μL) and perchloric acid buffer (100 μL)) were added to the biopsy sample and the mixture was homogenized with the help of a sonic dismembrator at speed of 5 for 10 seconds. The mixture was allowed to settle down and then additional perchloric acid buffer (50 μL)) was added. The mixture was vortexed and centrifuged at 12000 rpm at 23° C. for 5 minutes. The pellet and supernatant were separated. The supernatant was used for polyamine content determination via the N-dansylation procedure and the solid pellet was used for protein determination.

Protein Content of Tissue Sample.

The protein content of the remaining pellets were determined by the method of Lowry[16] after dissolution in 0.1N NaOH. The results were expressed in mg of protein.

Protocol for N-Dansylation of Polyamines.

The respective supernatants, which were collected above, were left in a freezer overnight, and then thawed to room temperature. To this solution, the internal standard (1,6-diaminohexane (STD, 5 in FIG. 1): 30 μL of $1.43 \times 10^{-4}$ M) was added followed by the addition of aq. $Na_2CO_3$ (200 μL of 1M aqueous solution/100 μL), and dansyl chloride (400 μL of a 5 mg/mL solution/100 μL). The reaction mixture was shaken on a rotary shaker at room temperature for 2 hours. A 1M proline solution (100 μL per 100 μL) was added and again the reaction mixture was shaken on a rotary shaker for 1 hr. Chloroform (2 mL) was added and the sample was shaken and the layers allowed to separate. The top water portion was removed by pipette and the chloroform layer was saved. The chloroform layer (~2 mL) was concentrated. The residue was dissolved in methanol (250 μL). Each sample was injected as its respective methanol solution (20 μL) and analyzed by HPLC using calibration curves determined with independently synthesized N-dansylated standards to provide the nmoles of each N-dansylated polyamine derivative. The HPLC polyamine quantification (nmol/mg protein) results are listed in Table 1.

Biopsy Methods.

Tissue biopsies used for polyamine extraction were obtained from RUSH University Gasteroenterology Tissue Repository. This Repository stores 6000 plus samples collected from IBD patients at −70° C. Relevant clinical data for these samples is stored in a database. For the purposes of this study, we used snap frozen endoscopic biopsies from 30 UC, 28 Crohns and 7 healthy subjects. Control subjects were those, who underwent surveillance colonoscopy and did not show any pathology during colonoscopy. For IBD patients, diagnosis was ascertained based on clinical data, endoscopy findings and histology findings. In IBD patients, biopsies were taken from inflamed and/or non-inflamed areas as indicated and appropriately labeled. Patients were considered to have active disease, if they were symptomatically positive, otherwise they were considered inactive. Blinded tissue samples were shipped to the University of Central Florida (UCF) in dry ice for polyamine extraction. The study was approved by both the UCF and RUSH University research and clinical affairs IRB committees.

Tissue Grading System Used.

To evaluate the degree of inflammation, the Weiss endoscopic index was used. 0=no signs of inflammation, 1=low degree of inflammation (increased granularity and friability of mucosa in UC and single small apthous lesion in Crohns), 2=moderate inflammation (mucous membranes, spontaneous bleeding and small ulcers in UC, multiple apthous lesions, and small ulcers in Crohns). 3=severe Inflammation (large ulcers in UC and large ulcerous lesions in Crohns).

Statistical Analysis.

MS Excel and SAS v8.2 was used to perform ANOVA (Analysis of variance) and Fisher's LSD test. Data is expressed as Means+/−SEM. Differences were considered significant when $P<0.05$.

Results.

Figure 3:
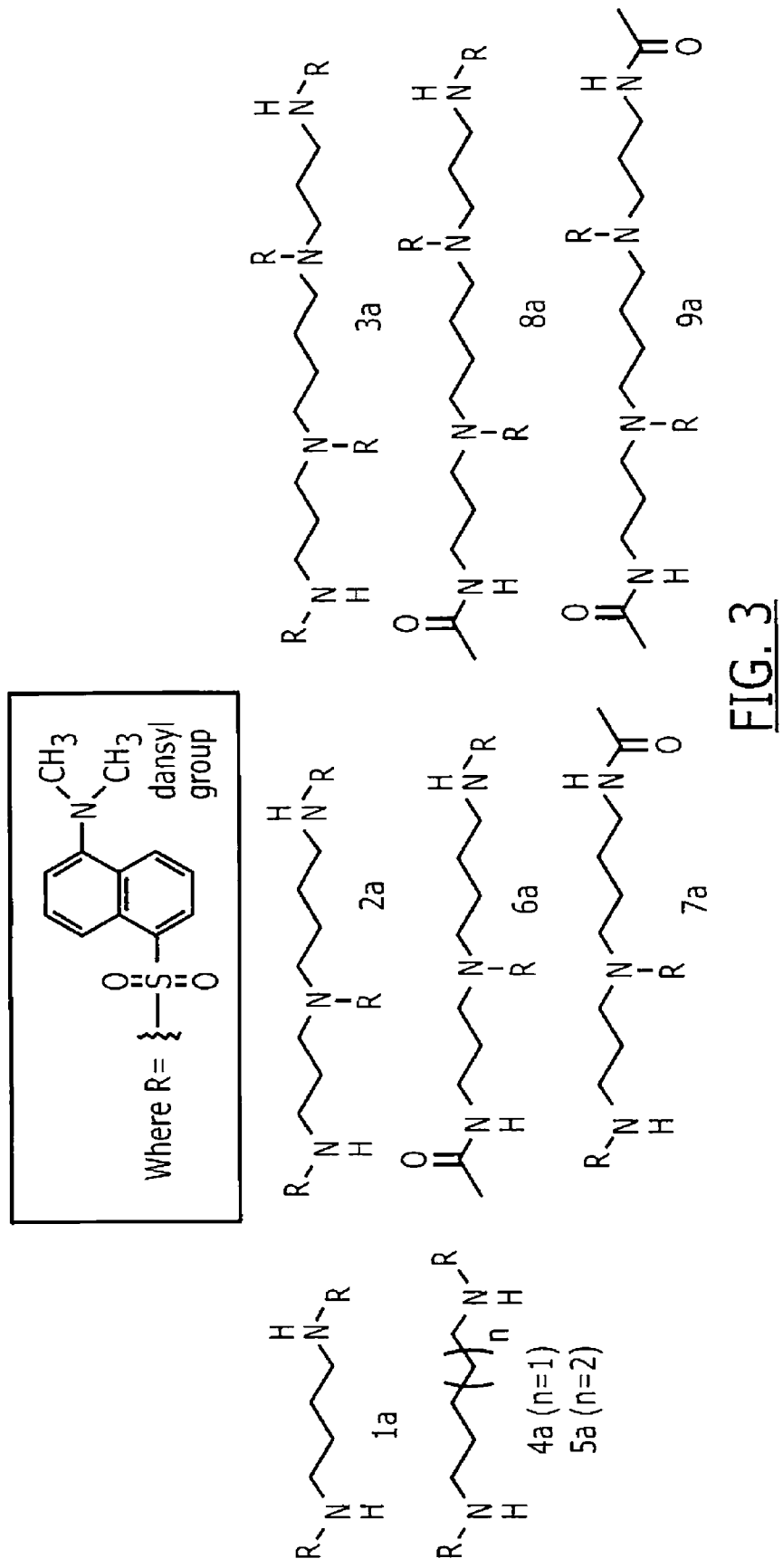

Each of the N-dansylated derivatives shown in FIG. 3 were synthesized, purified and characterized (see Experimental). A modified HPLC protocol with fluorescence detection was developed to separate and quantify these nine derivatives. Since 6a and 7a were positional isomers, they are difficult to resolve in most cases. Since their respective molar response was very similar, the area % s of these two merged peaks were combined and listed tallied as '6a+7a' and represents the total mono-N-acetylspermidine population (i.e., 6 and 7).

Figure 4:
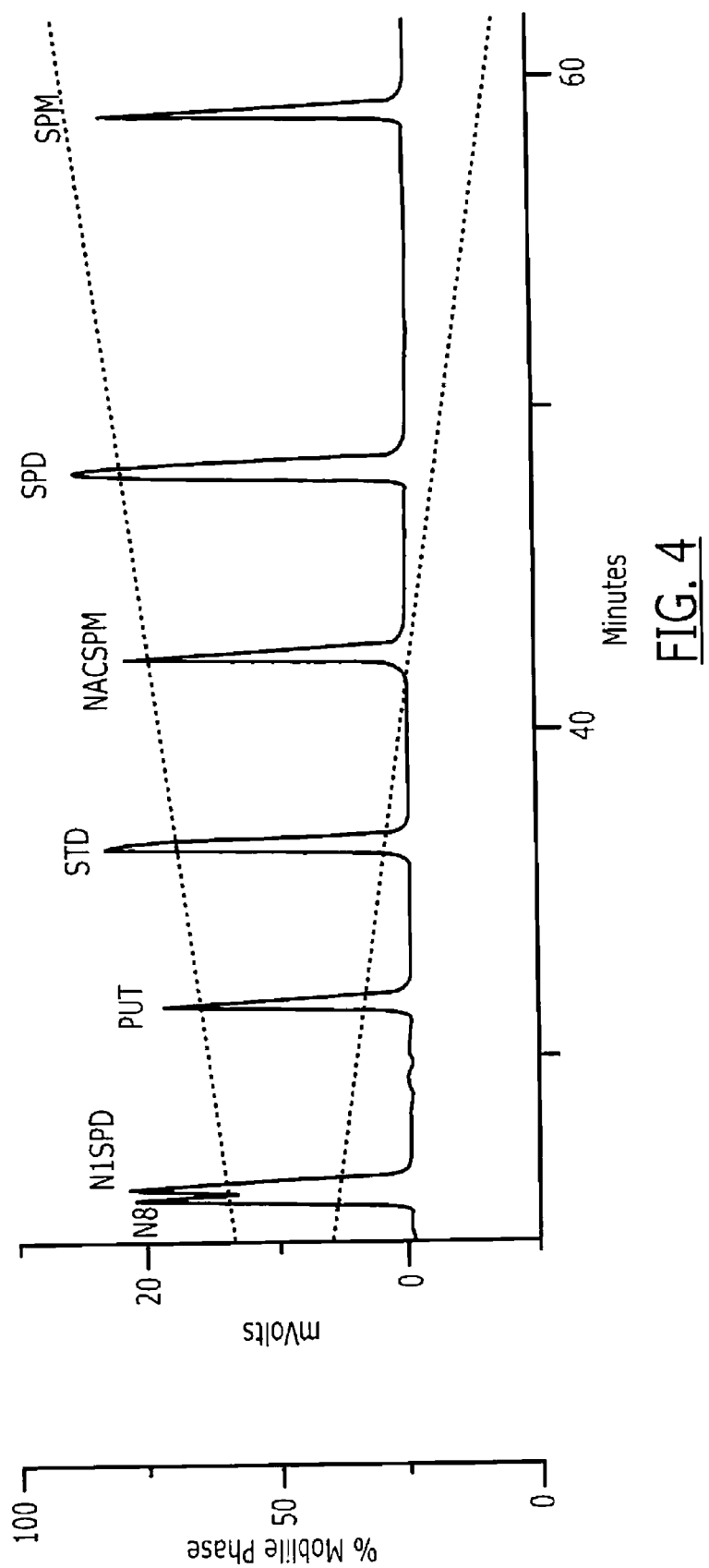
FIG. 4 is a graph showing sample HPLC trace of N-dansylated derivatives (respectively from left to right: 7a, 6a, 1a, 5a, 8a, 2a, and 3a)

Technically speaking, the HPLC method quantifies each of the N-dansylated polyamine derivatives (e.g., 1a). However, the number of nmoles of the N-dansyl derivative (e.g., 1a) is directly equal to the number of nmoles of free polyamine from which it was derived (i.e., 1) because the yield in the N-dansylation reactions was nearly quantitative (~98%). Therefore, discussions and comparisons pertaining to the N-dansylated derivatives (1a-9a) directly apply to their respective free polyamine forms as well (1-9). A sample HPLC trace is shown in FIG. 4. Due to their direct molar relationship and to simplify the discussion, the measured HPLC levels will be referred to as their non-dansylated free polyamine forms, although technically the measured values shown in the Tables are from the respective N-dansylated derivatives.

Cadaverine (CAD, 4) exists in most bacteria and is synthesized by the degradation of L-lysine by lysine decarboxylase.[17, 18] To the best of our knowledge, cadaverine 4 is not synthesized in human cells. As such, the detection of cadaverine 4 indicates the presence of bacterial contaminants in the tissue samples collected, even though the tissues were washed extensively before analysis. Therefore, cadaverine provides an important cross-check and control for bacterial contributions to the polyamine pools. Of the initial 58 samples collected, nine samples had cadaverine 4 present and were removed from the study. This was an essential step for our subsequent analyses as gut flora also produce polyamines and may have skewed the results if these samples had been included. In short, each of the samples presented in the Tables and discussed in this report had no detectable cadaverine 4 present (as measured by our HPLC protocol) and were deemed 'bacteria-free'. In this regard, our conclusions are from the human tissue analyzed.

Intestinal Mucosal Polyamine Levels in Healthy Subjects.

The first experiments determined the baseline PA levels in healthy ileum and sigmoid tissues. As shown in Table 1, no significant differences were observed in the small and large bowel samples collected. As expected, the pattern of PA levels in these two sites were very similar with CNAcSPD (combination of 6+7) being the highest and with NAcSPM (8) being undetectable in these healthy samples. Table 1 shows the amount of polyamines (in nmoles/mg of protein) found in each of the samples tested.

TABLE 1

Polyamine levels in colonic mucosa from the ileum and sigmoid of healthy subjects (values are listed in nmoles/mg protein)

| Site | n | PUT (1) | SPD (2) | SPM (3) | CNAcSPD (6 + 7) | NAcSPM (8) |
|---|---|---|---|---|---|---|
| Ileum control | 3 | 0.45 ± 0.45 | 1.73 ± 0.32 | 3.30 ± 1.69 | 9.45 ± 4.72 | 0.00 ± 0.00 |
| Sigmoid control | 4 | 0.53 ± 0.53 | 3.06 ± 1.20 | 5.46 ± 2.05 | 12.51 ± 6.28 | 0.00 ± 0.00 |

Association of Inflammatory Bowel Disease (IBD) with Elevated Tissue Polyamine Levels Armed with the above controls, we determined the polyamine levels of the ileal and sigmoid mucosal biopsies obtained during endoscopic procedures from healthy subjects and patients with active and inactive IBD (ulcerative colitis and Crohn's disease). The seven control samples in Table 1 were averaged and combined to provide the Control values in Table 2 for comparison to the average polyamine (PA) levels measured in the collected IBD samples. As such, Table 2 gives an overview of healthy vs. IBD associated PA levels.

TABLE 2

Polyamine (nmoles/mg protein) levels in healthy and IBD tissues

| Diagnosis | n | PUT (1) | SPD (2) | SPM (3) | CNAcSPD (6 + 7) | NAcSPM (8) |
|---|---|---|---|---|---|---|
| Control | 7 | 0.50 ± 0.33 | 2.49 ± 0.71 | 4.53 ± 1.34 | 11.19 ± 3.85 | 0.00 ± 0.00 |
| IBD | 49 | 0.70 ± 0.22 | 3.55 ± 0.55 | 6.11 ± 0.62 | 9.95 ± 2.09 | 0.04 ± 0.02 |

As shown in Table 2, the IBD polyamine levels for 1, 2, 3 and 6+7 were not statistically different from the healthy samples with the lone exception of 8, i.e., $N^1$-acetylated spermine.

As will be discussed below, compound 8 is involved in intracellular polyamine catabolism. Intracellular polyamine levels are tightly regulated by a negative feedback control mechanism involving a balance between PA biosynthesis and catabolism. For example, spermine 3 is converted into acetyl derivative 8 by the action of SSAT (spermine-spermidine acetyl transferase). In turn, 8 is converted to spermidine 2 via the action of polyamine oxidase. In this regard, 8 represents an important metabolite generated by cells in response to high intracellular spermine levels and/or high SSAT activity. The fact that this compound was undetected in healthy tissues suggests that 8 may represent a new biomarker for tracking IBD activity and progression.

Correlation of Active Inflammation with Elevated Tissue Polyamines

Figure 1:
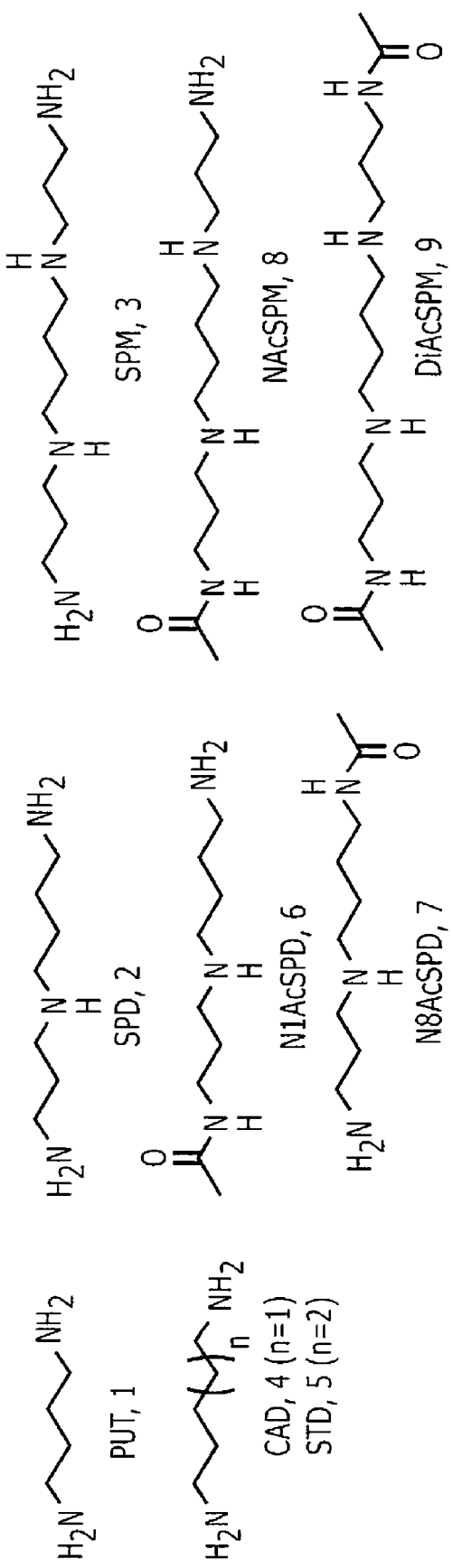
FIG. 1 shows structures of polyamines and metabolites: putrescine 1, spermidine 2, spermine 3, cadaverine 4, 1,6-hexanediamine HPLC standard 5, N1-acetylated spermidine 6, N8-acetylated spermidine 7, N1-acetylated spermine 8, and N1,N12-diacetylated spermine 9, all as known in the art.

To see if active, ongoing inflammation affected tissue PA levels, we compared values from symptomatic patients with active IBD, asymptomatic inactive IBD (based on standard clinical disease activity indices) and controls. As shown in Table 3 and FIG. 1, tissue levels of SPD 2, SPM 3 and NAcSPM 8 were significantly elevated in patients with active IBD compared to inactive IBD and controls. Tissue levels of PUT 1 and CNAcSPD (6+7) were not significantly different among three groups (FIG. 1). There was no significant differences in the mean PA levels between patients with inactive IBD and the controls. This early observation suggested that elevated tissue levels of 2, 3 and 8 may be due to active inflammation and may not be specific for IBD per se.

TABLE 3

Polyamine levels in healthy vs inactive and active IBD tissues

| Activity | n | PUT (1) | SPD (2) | SPM (3) | CNAcSPD (6 + 7) | NAcSPM (8) |
|---|---|---|---|---|---|---|
| Control | 7 | 0.50 ± 0.33 | 2.49 ± 0.71 | 4.53 ± 1.34 | 11.19 ± 3.85 | 0.00 ± 0.00 |
| Inactive IBD | 26 | 0.63 ± 0.36 | 2.27 ± 0.24 | 4.99 ± 0.34 | 9.00 ± 2.16 | 0.00 ± 0.00 |
| Active IBD | 23 | 0.78 ± 0.22 | 5.00 ± 1.08** | 7.39 ± 1.23** | 11.03 ± 3.78 | 0.09 ± 0.05** |

**indicates significant difference from inactive IBD with $p < 0.05$

Note: Table 3 is also shown as a bar graph in FIG. 1 for comparison.

Tissue Injury and Elevation of Tissue Polyamines in Patients with Active IBD

In order to determine whether elevated tissue polyamines in symptomatic patients with active IBD represent tissue injury, we used endoscopy as an assessment tool to assign tissue samples as being "involved" (injured) vs. "non-involved" (normal), regardless of whether patients had clinically active disease or not. In this manner, we compared polyamine (PA) levels in tissues, which appeared via endoscopy to be injured (involved) tissues, to PA levels in tissues which appeared to be normal mucosa.

PA levels did not correlate with tissue 'involvement' in the terminal ileum samples tested. As shown in FIG. 2, SPD levels in 'Involved Sigmoid' were significantly higher than in 'Non involved Sigmoid' (FIG. 2: SPD 4.59±0.58 vs. 2.68±0.33 nmol/mg protein). However, the SPD level was not statistically higher than the control value when one takes into account the error of the measurement (FIG. 2). Nevertheless, this finding indicated that SPD levels in sigmoid biopsies may provide an additional indication of active IBD disease and correlated with the endoscopic indicators of inflammation.

The results depicted in FIGS. 1 and 2 suggest that spermidine (SPD) levels were increased in symptomatic patients with active IBD and more specifically in the macroscopically-'involved' mucosa. To see if the combination of clinical activity and endoscopic 'involvement' correlated with PA levels, we compared the PA levels in endoscopically 'involved' samples to the levels in 'non-involved' mucosa in patients with active and inactive IBD. These findings are listed in Table 4.

An analysis of variance showed significantly raised SPD 2, SPM 3 and NAcSPM 8 levels in the active "non-involved" IBD group as compared to inactive "non-involved" IBD group (Table 4). This result with the 'non-involved' samples (which appear normal via endoscopy) indicates that increased levels of 2, 3 and 8 track well with the clinical activity of IBD even when the biopsy site appears to be normal. In short, tissue samples, which appeared endoscopically normal (non-involved) from patients with clinically-active IBD, had statistically significant higher levels of these three polyamines (2, 3 and 8).

A comparison of active 'involved' IBD versus inactive 'involved' IBD also showed significantly higher levels of 2 (4.64±0.41 vs. 2.81±0.77 nmol/mg protein) for the clinically-active IBD subjects over their clinically inactive counterparts, respectively. If inflammation (or the degree of 'involvement') alone explained the findings, then one would have expected these latter two "involved" entries to have similar SPD levels. Clearly, this was not the case. The significant difference observed suggested that the 'involvement' or inflammation alone did not explain the high SPD levels.

Overall, the clinically-active IBD samples consistently had higher levels of SPD than the clinically-inactive group. Collectively, these findings support the conclusion that tissue SPD levels are significantly increased in clinically-active IBD patients regardless of whether the biopsy site is visibly injured or visibly assigned as normal colonic mucosa.

TABLE 4

Effect of clinical activity and endoscopic involvement of the gut on colonic mucosal polyamine levels (nmoles/mg of protein)

| Group | n | PUT 1 | SPD 2 | SPM 3 | CNAcSPD (6 + 7) | NAcSPM 8 |
| --- | --- | --- | --- | --- | --- | --- |
| Control | 7 | 0.50 +/− 0.33 | 2.49 +/− 0.71 | 4.53 +/− 1.34 | 11.19 +/− 3.85 | 0.00 +/− 0.00 |
| Inactive Non-Involved IBD | 22 | 0.70 +/− 0.42 | 2.18 +/− 0.25 | 5.03 +/− 0.33 | 9.50 +/− 2.54 | 0.00 +/− 0.00 |
| Inactive Involved IBD | 4 | 0.26 +/− 0.26 | 2.81 +/− 0.77 | 4.74 +/− 1.38 | 6.25 +/− 1.04 | 0.00 +/− 0.00 |
| Active Non-involved IBD | 12 | 0.74 +/− 0.32 | 5.33 +/− 2.08* | 8.34 +/− 2.21* | 15.09 +/− 7.07 | 0.11 +/− 0.07* |
| Active Involved IBD | 11 | 0.82 +/− 0.32 | 4.64 +/− 0.41** | 6.35 +/− 0.90 | 6.60 +/− 1.42 | 0.07 +/− 0.07 |

*indicates a statistical significant difference from Inactive Non-involved IBD group with $p < 0.05$.
**indicates a statistical significant difference from Inactive Involved IBD group with $p < 0.05$.

PA Tissue Levels in Ulcerative Colitis (UC) and Crohn's Disease (CD)

To this end, we initially compared the tissue PA levels in patients with UC and patients with CD to values from healthy subjects and then compared the values between UC and CD.

Ulcerative Colitis (UC) Findings.

As expected, the polyamine levels in non-involved ileum from UC patients were similar to normal ileum from healthy subjects (Table 5). Moreover, there was no significant difference in the mean PA levels between inactive UC and the sigmoid control (Table 6 and FIG. 3A). In contrast, the mean SPD levels were significantly higher in active UC compared to inactive UC and controls (Table 6 and FIG. 3A). The tissue levels of the other polyamines in patients with active UC were similar to the control group (Table 6). However, it is interesting to note that compound 8 was detected in the active UC samples but not in the inactive UC tissues or the sigmoid control.

TABLE 5

Polyamine levels in the ileal mucosa of healthy subjects and patients with ulcerative colitis (nmoles/mg protein).

| Diagnosis | Site | n | PUT (1) | SPD (2) | SPM (3) | CNAcSPD (6 + 7) | NAcSPM (8) |
| --- | --- | --- | --- | --- | --- | --- | --- |
| Control | Ileum control | 3 | 0.45 ± 0.45 | 1.73 ± 0.32 | 3.30 ± 1.69 | 9.45 ± 4.72 | 0.00 ± 0.00 |
| Inactive IBD | Non-involved ileum | 4 | 0.60 ± 0.40 | 2.40 ± 0.43 | 5.23 ± 0.33 | 9.52 ± 2.61 | 0.00 ± 0.00 |

TABLE 6

Polyamine levels in the sigmoid mucosa of healthy subjects and patients with ulcerative colitis (nmoles/mg protein)

| Activity | n | Put (1) | SPD (2) | SPM (3) | CNAcSPD (6 + 7) | NAcSPM (8) |
|---|---|---|---|---|---|---|
| Sigmoid Control | 4 | 0.53 ± 0.53 | 3.06 ± 1.20 | 5.46 ± 2.05 | 12.51 ± 6.28 | 0.00 ± 0.00 |
| Inactive UC | 12 | 0.83 ± 0.76 | 2.59 ± 0.45 | 4.67 ± 0.66 | 11.35 ± 4.52 | 0.00 ± 0.00 |
| Active UC | 6 | 0.44 ± 0.20 | 4.64 ± 0.62** | 5.97 ± 0.64 | 8.73 ± 1.62 | 0.09 ± 0.09 |

**indicates a statistically significant difference from inactive UC with p < 0.05

A further analysis of variance for UC based on endoscopic involvement did not show any significant differences in the PA levels (FIG. 3B).

Crohns Disease (CD) Findings: Tissue Polyamine Levels in Crohn's Disease.

Ileum CD.

Regardless of whether the biopsy site was endoscopically assigned as 'involved' or 'non-involved,' the polyamine levels in the ileum of CD patients were similar to controls (FIG. 4A). There were no statistically significant trends observed in FIG. 4A.

However, when the samples were assessed via their clinical activity (i.e. active inflammation) SPD and SPM levels in ileal tissue of clinically-active CD patients were significantly higher than those of inactive CD patients and the ileal control as shown in FIG. 4B. This indicates that SPD and SPM levels are increased in the inflamed injured mucosa. The other PA levels in the active Heal samples (1, 6+7, and 8) were not statistically different from the ileal controls (FIG. 4B).

Figure 5:
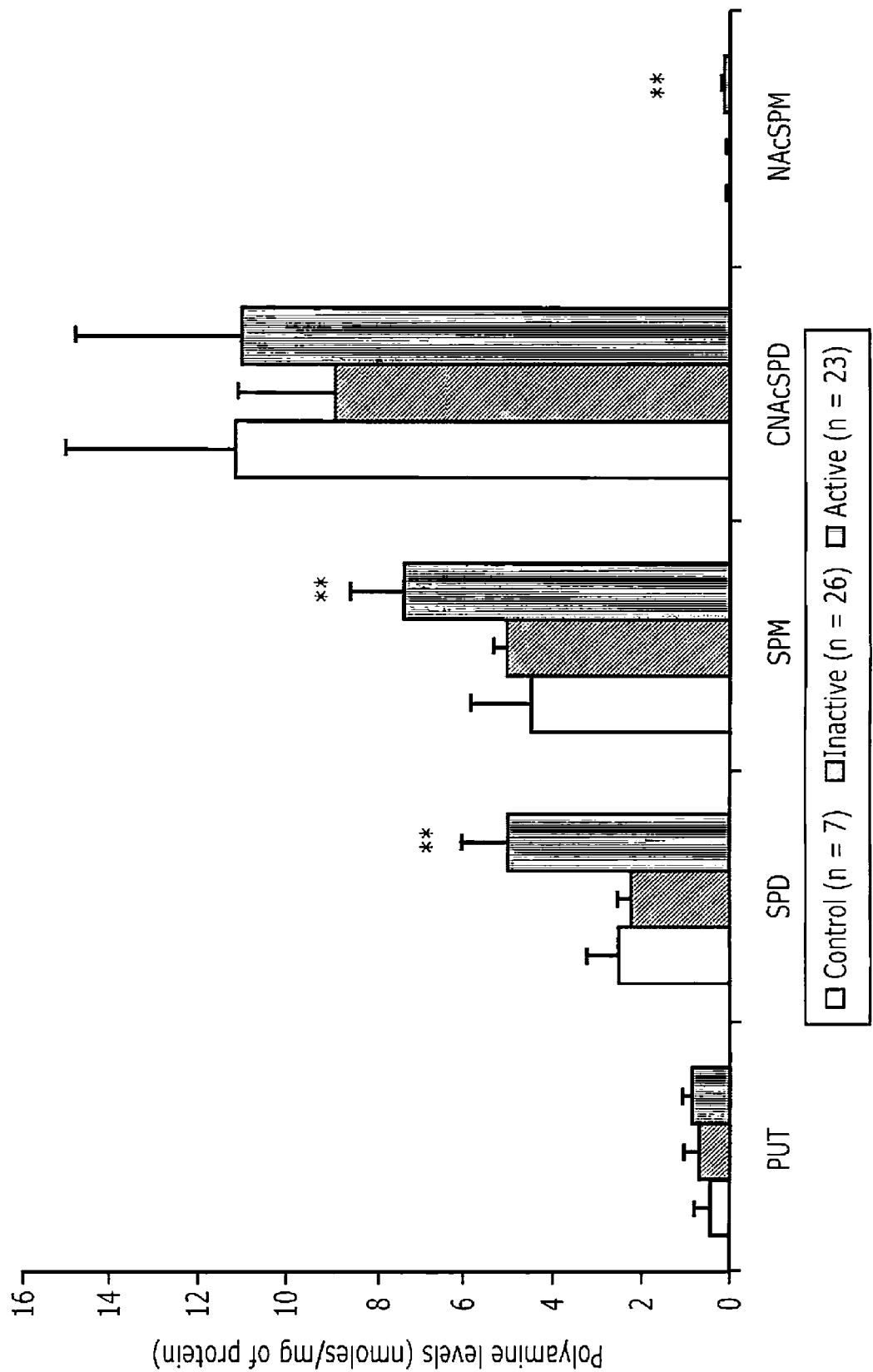
FIG. 5 is a bar graph showing the effect of active inflammation of the gut on tissue polyamine homeostasis.

Sigmoid CD. SPD levels in the 'involved' sigmoid tissue of CD patients were higher than the corresponding 'non-involved' sigmoid tissue (FIG. 5A). However, the SPD level was not significantly different than the sigmoid control (FIG. 5A). Of particular note was that 8 was detected in the involved CD sigmoid tissue and not in the sigmoid control (FIG. 5A).

When the samples were assessed via their clinical activity (i.e. active inflammation) again SPD was statistically significantly higher in active CD tissue than in the inactive CD tissues. However, the SPD level in active CD tissue was not significantly different than the sigmoid control (FIG. 5B). The other PA levels in active Crohn's patients were similar to the values obtained from healthy controls and inactive patients with the exception of 8. Compound 8 was detected in active CD tissue and not in the control or inactive CD tissue (FIG. 5B). Lastly, we investigated whether there was a difference between CD and UC in tissue polyamines levels. To determine whether changes in tissue PA levels noted in IBD patients were specific for the types of IBD, we compared the tissue values in UC and CD patients. As depicted in Table 7a-c, there were no significant differences in polyamine levels between tissues from UC and Crohn's patients with the exception of the observed higher SPD 2 and CNAcSPD (6+7) levels in inactive UC tissues over the inactive Crohns tissue (Table 7b).

TABLE 7a

Crohns vs UC (nmoles/mg protein)

| Diagnosis | n | PUT | SPD | SPM | CNAcSPD | NAcSPM |
|---|---|---|---|---|---|---|
| Crohns | 14 | 0.71 +/− 0.24 | 3.14 +/− 0.52 | 6.45 +/− 0.70 | 6.94 +/− 1.64 | 0.11 +/− 0.07 |
| UC | 18 | 0.70 +/− 0.51 | 3.27 +/− 0.42 | 5.11 +/− 0.50 | 10.48 +/− 3.03 | 0.03 +/− 0.03 |

TABLE 7b

Inactive Crohns vs Inactive UC (nmoles/mg protein)

| Group | n | PUT | SPD | SPM | CNAcSPD | NAcSPM |
|---|---|---|---|---|---|---|
| Crohns Inactive | 5 | 0.60 +/− 0.37 | 1.62 +/− 0.43 | 5.19 +/− 0.55 | 4.58 +/− 1.44 | 0.00 +/− 0.00 |
| UC Inactive | 12 | 0.83 +/− 0.76 | 2.59 +/− 0.45** | 4.67 +/− 0.66 | 11.35 +/− 4.52** | 0.00 +/− 0.00 |

**denotes a statistically significant difference from Crohns inactive group with p < 0.05

TABLE 7c

Active Crohns vs Active UC (nmoles/mg protein)

| Group | n | PUT | SPD | SPM | CNAcSPD | NAcSPM |
|---|---|---|---|---|---|---|
| Crohns Active | 9 | 0.78 +/− 0.32 | 3.98 +/− 0.61 | 7.15 +/− 1.00 | 8.25 +/− 2.38 | 0.17 +/− 0.11 |
| UC Active | 6 | 0.44 +/− 0.20 | 4.64 +/− 0.62 | 5.97 +/− 0.64 | 8.73 +/− 1.62 | 0.09 +/− 0.09 |

Summary of Results.

In a comparison between IBD vs healthy tissues, the level of compound 8 was significantly higher in IBD tissues and was not detected in the control healthy tissues. When the IBD tissues were segregated into clinically active and inactive categories, the IBD active tissues revealed increased levels of SPD 2, SPM 3 and NAcSPM 8. Clinical activity tracked well with increased SPD levels regardless of whether the tissue appeared inflamed or normal by endoscopy (Table 4). Active UC gave statistically higher SPD levels than either inactive UC tissue or the sigmoid control (Table 6). Compound 8 was detected in active UC tissues and not in the control samples. Active CD gave higher SPD and SPM levels than inactive CD tissues and the ileal control. The CD sigmoid results were equivocal except for the fact that 8 was detected in the involved sigmoid but not in the control. No difference between UC and CD samples were observed except that higher levels of SPD and NAcSPD (6+7) were noted in the inactive UC over the inactive CD tissues (Table 7b). In summary, both SPD 2 and compound 8 represent useful tools to track IBD progression especially in the ileal samples of CD patients and the colonic samples of UC patients.

Discussion.

Polyamine metabolism. Polyamine levels are tightly regulated in cells and there is an exquisite balance between polyamine biosynthesis via ODC and polyamine catabolism via SSAT and PAO action.[18-21] As shown in Scheme 1, polyamine biosynthesis starts primarily with the decarboxylation of ornithine to form putrescine 1.[20] Spermidine synthase then aminopropylates one end of 1 to form spermidine 2. Likewise, spermine synthase then aminopropylates the butylamino end of 2 to form spermine 3. In this stepwise manner, cells build the higher polyamines 2 and 3 from their putrescine precursor, 1.[20] Note: the aminopropylation fragment is donated by decarboxylated S-adenosyl-methionine (dcSAM), which is generated by the action of adenosyl methionine decarboxylase (SAMDC) on S-adenosyl-methionine (SAM).[20]

Polyamine catabolism or breakdown mainly occurs by the action of spermidine/spermine acetyl transferase (SSAT), which N-acetylates one of the terminal ends of the polyamine chain.[20] For example, the action of SSAT on spermidine 2 results in 6, whereas the action of SSAT on spermine 3 results in 8. The acetylated adducts 6 and 8 are excreted by the cell or oxidized by polyamine oxidase (PAO), a flavin adenine dinucleotide-dependent enzyme into putrescine 1 and spermidine 2, respectively. The other oxidation byproducts are hydrogen peroxide 10 and 3-acetaminopropanol 11.[20]

Therefore, high intracellular levels of SPM 3 would be converted to NAcSPM 8 by SSAT and eventually converted to SPD 2 via PAO activity. In this regard, this study is the first observation of both high SPD 2 and high $N^1$-acetylspermine, NAcSPM 8 in UC tissues. The fact that the levels of 2 and 8 are significantly higher than the controls supports our premise of high intracellular polyamine levels.

The current SPD results are consistent with those observed by Obayashi, who also noted high SPD levels in UC patients.[21] Moreover, Obayashi concluded that the high spermidine levels in cells were "not due to changes in the synthesis or degradation of polyamines" but due to "increased exogenous spermidine uptake".[21] High polyamine uptake via PAT would raise intracellular polyamine levels. However, Weiss et al using isolated colonic epithelial cells (CECs) from patients with severe ulcerative colitis observed a lack of the anti-inflammatory polyamine, spermine 3.[22] Weiss also observed increased levels of spermidine and $N^8$-acetylspermidine 7 and rationalized the findings by stating that the increased levels may be due to increased uptake and metabolism due to accelerated proliferation of CECs. The current findings identified 8 as another potential marker for this disease and may explain the lack of 3 in Weiss' study. Hypothetically, if polyamine metabolism (i.e., SSAT activity) is high in UC tissues then 3 would be converted to 8, a spermine metabolite (Scheme 1).

Putting these observations together, high PAT activity leads to high levels of SPD in UC tissues. Ingestion of these polyamine-rich cells by macrophages reduces their phagocytotic ability and facilitates disease progression (FIG. 2).

Macrophages. Macrophages are derived from specific white blood cells called monocytes.[10, 11] Monocytes and macrophages are phagocytes, which engulf and digest pathogens and rouge cells present in tissues. They provide innate immunity and can also be involved in specific cell-mediated defense. Unlike the early responding neutrophils, which have a short life span (days), macrophages can live for months (to years) and are attracted to damaged tissue via chemotaxis (e.g., via chemical attractants such as histamine and released cytokines). A macrophage ingests its target via formation of an intracellular compartment known as a phagosome. The phagosome then fuses with a lysosome, which uses digestive enzymes to destroy the pathogen. After digestion, a common antigen found on the surface of the pathogen will be positioned on the surface of the macrophage as a MHC class II complex.

Even though previous authors have demonstrated the relationship between macrophages and polyamines,[10, 11] further studies are needed to see if high levels of spermidine 2 (or N-acetylated spermine 8) in UC tissues causes defective macrophage function in UC patients.

Although not obtained in UC patients per se, there are several observations, which support our premise. First, Bulychev et al have already demonstrated that spermidine 2 can alter the structure and lower the phagocytotic activity of aveolar macrophages.[11] Second, high spermidine levels have been observed in IBD-related macrophages and monocytes.[23] Specifically, initial results revealed high SPD levels in Crohns mono-nuclear cells (MNCs) in support of this premise. Moreover, macrophages isolated from Crohns patients had lowered phagocytotic activity.[23]

Lastly, as shown in Table 8, MNCs were isolated from the blood of Crohns patients and healthy subjects and the levels of SPD and SPM were determined by the HPLC protocol. Indeed, our data revealed high spermidine (SPD) levels in the circulating mononuclear cells of Crohns patients. A related finding was also found by Obayashi in the mucosa of active ulcerative colitis (UC) patients.[21]

TABLE 8

Polyamine levels (nmol/mg protein) in mononuclear cells (MNC).

| | SPD (2) | SPM (3) |
|---|---|---|
| Healthy Persons (n = 6) | | |
| MNC | 0.09-0.23 | 0.24-0.57 |
| Crohns Patients (n = 2) | | |
| MNC | 0.41-0.67** | 0.37-0.66 |

Collectively, these observations indicate that polyamine metabolism and transport may be involved in UC progression (and possibly IBD in general). Indeed, the high polyamine content of inflamed IBD tissues (e.g. 2) may result in a reduced innate immune response by limiting the phagocytotic activity of circulating macrophages. While more work is needed in this area, the relationship between polyamines, inflammation and IBD continues to an area ripe for investigation.[20] Once confirmed, the IBD community will at last have a possible etiology for UC. Moreover, if polyamine transport is the cause of high intracellular polyamine levels, then PAT inhibitors[24] and special diets[25] may offer a novel therapy/treatment for UC patients.

In summary, the findings that both N-acetylated spermine 8 and spermidine 2 are elevated in UC tissues suggest not only a potential new biomarker for UC (e.g., 8), but also 'earmarks' the role of polyamine metabolism in IBD progression for future study.

Figure 6:
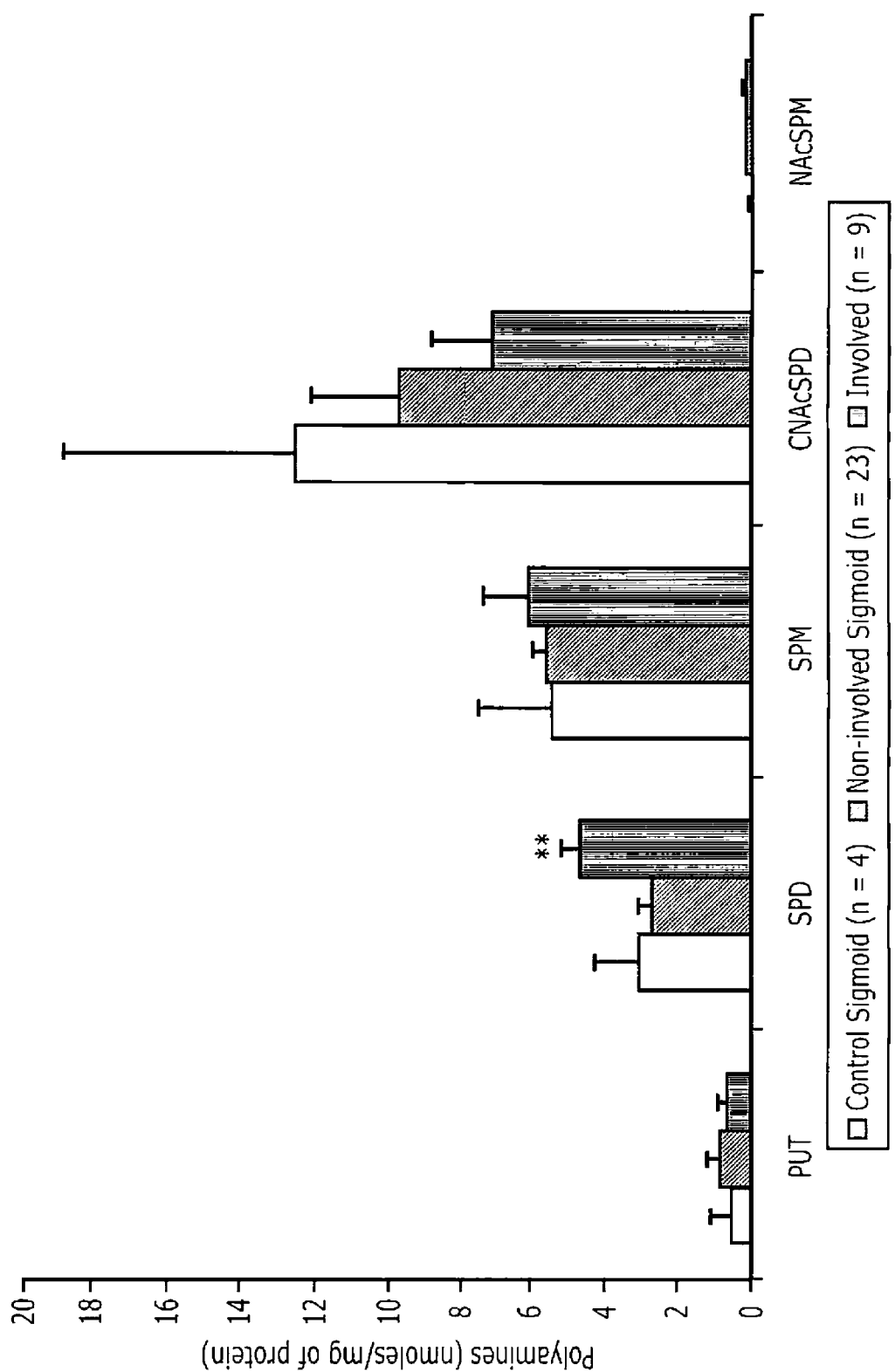
FIG. 6 presents a bar graph showing mean polyamine levels in sigmoid biopsies from patients with Inflammatory bowel disease and healthy controls.
Figure 7:
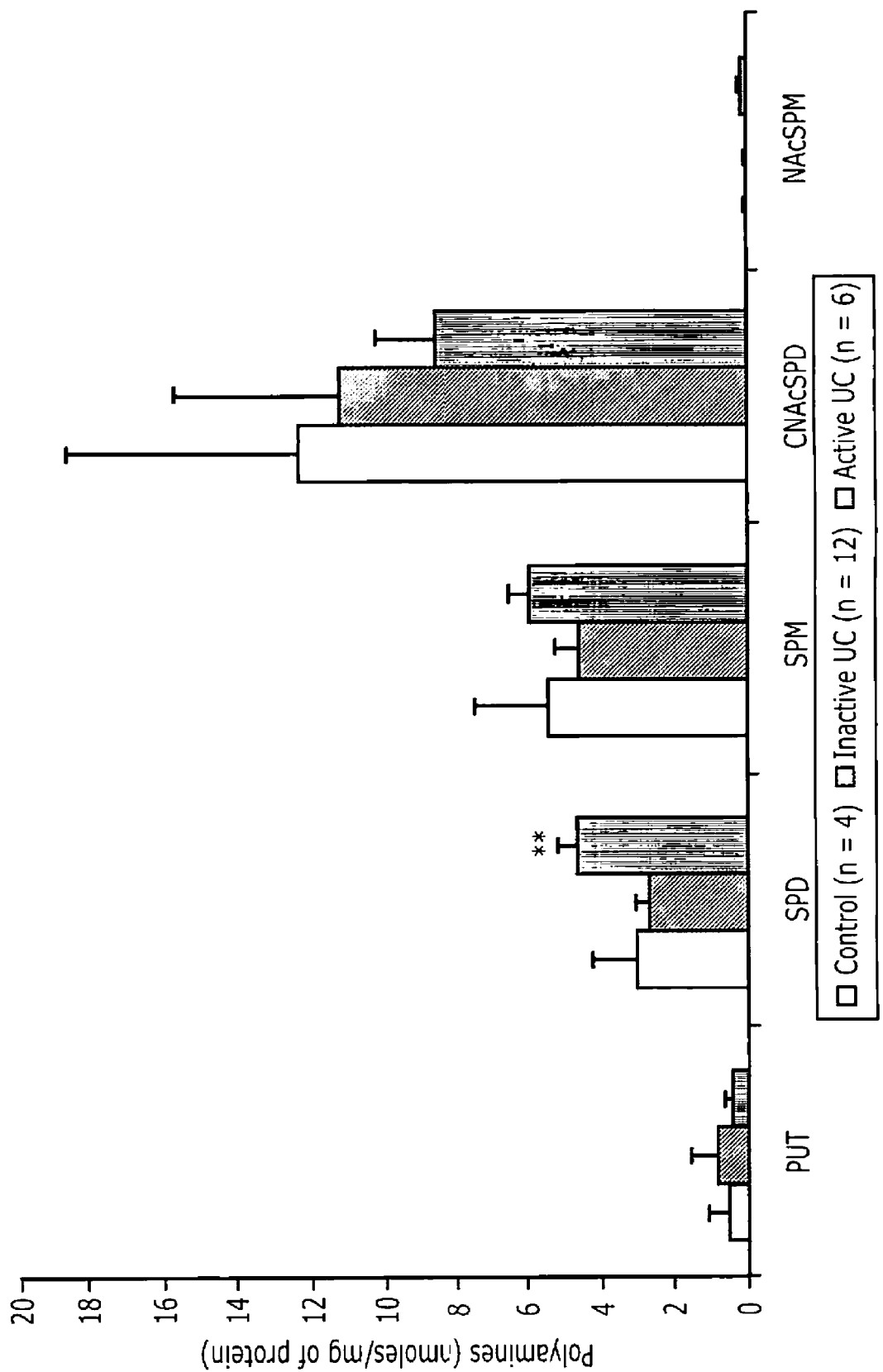
FIG. 7 shows the effect of active inflammation on polyamine levels in sigmoid tissue from Ulcerative Colitis subjects compared to healthy controls.
Figure 8:
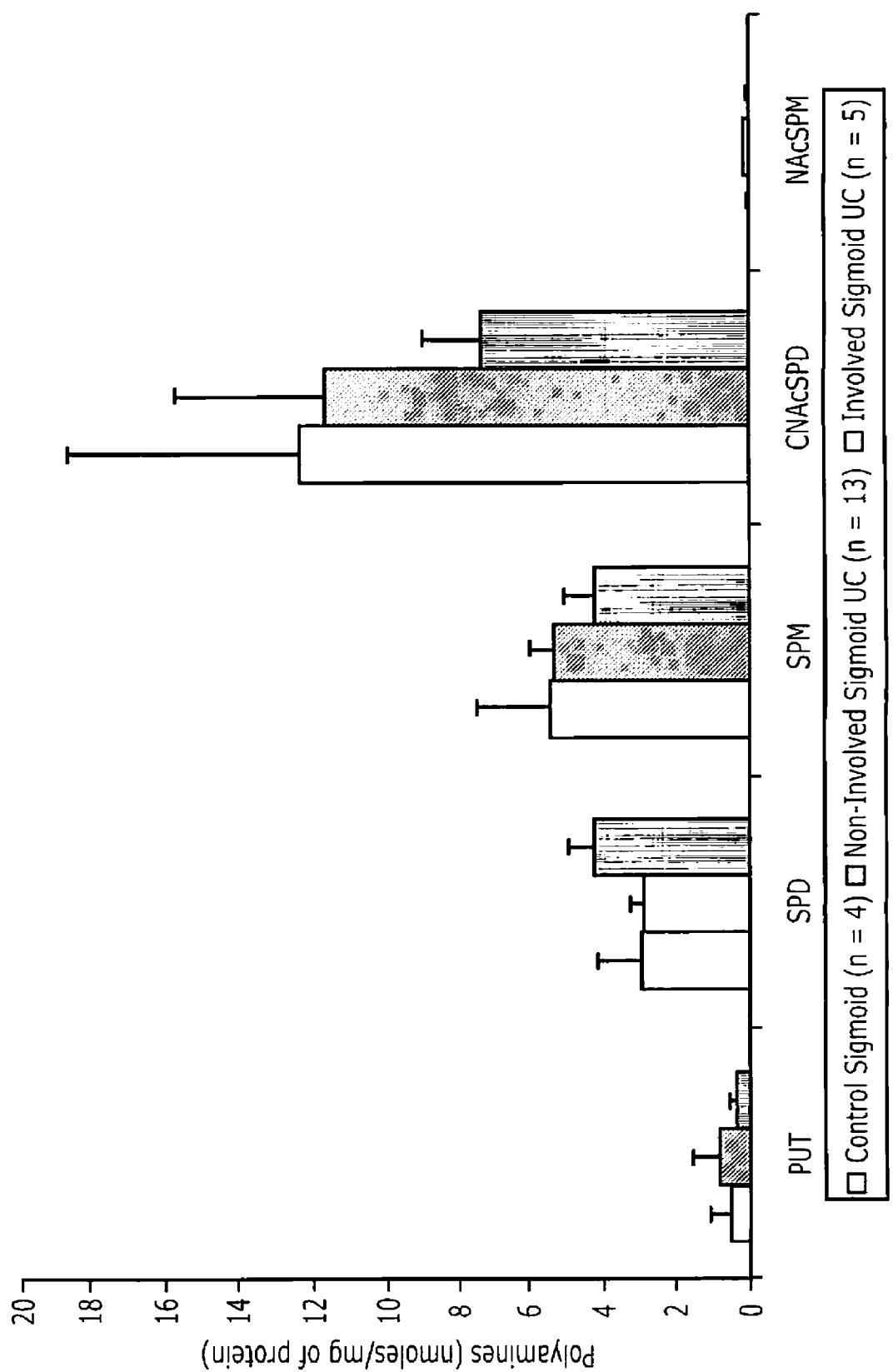
FIG. 8 depicts the effect of involvement (as evaluated by endoscopic examination) of sigmoid tissue on PA levels in sigmoid tissue in UC subjects.
Figure 9:
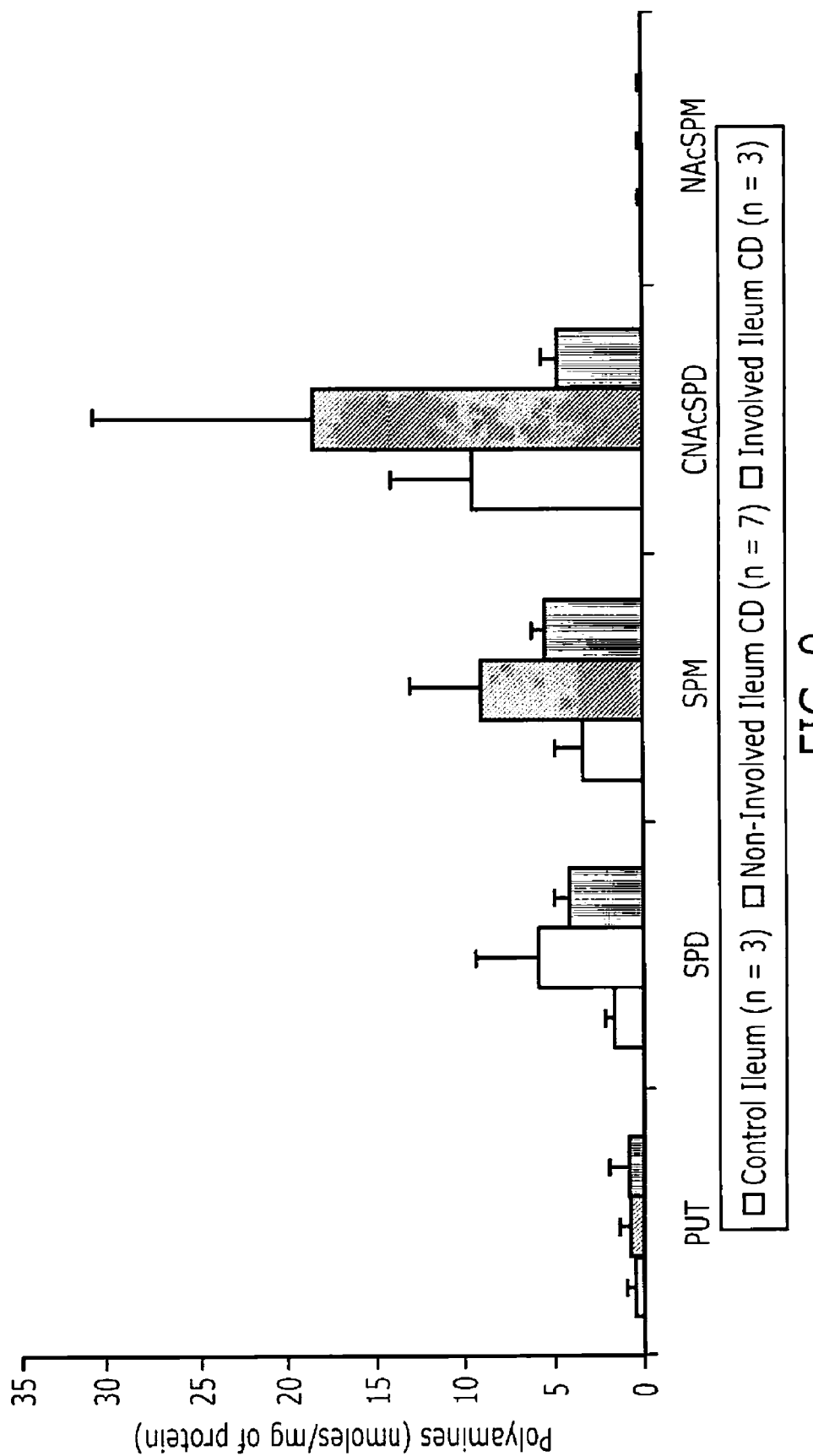
FIG. 9 portrays in a bar graph the effect of tissue involvement on PA levels in the Ileum of Crohns disease subjects.
Figure 10:
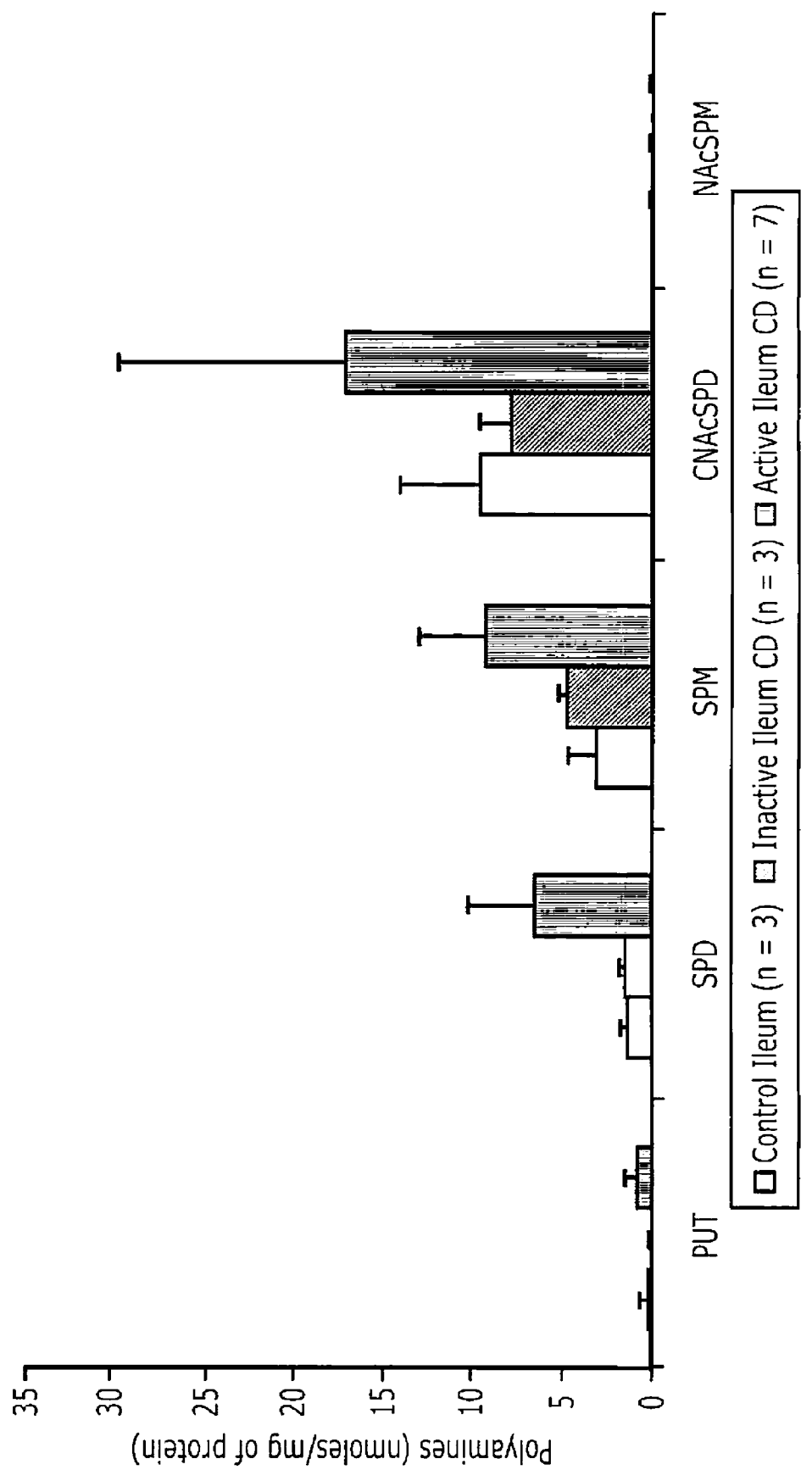
FIG. 10 shows the effect of 'clinically-active' inflammation on PA levels in the Ileum of Crohns disease subjects.
Figure 11:
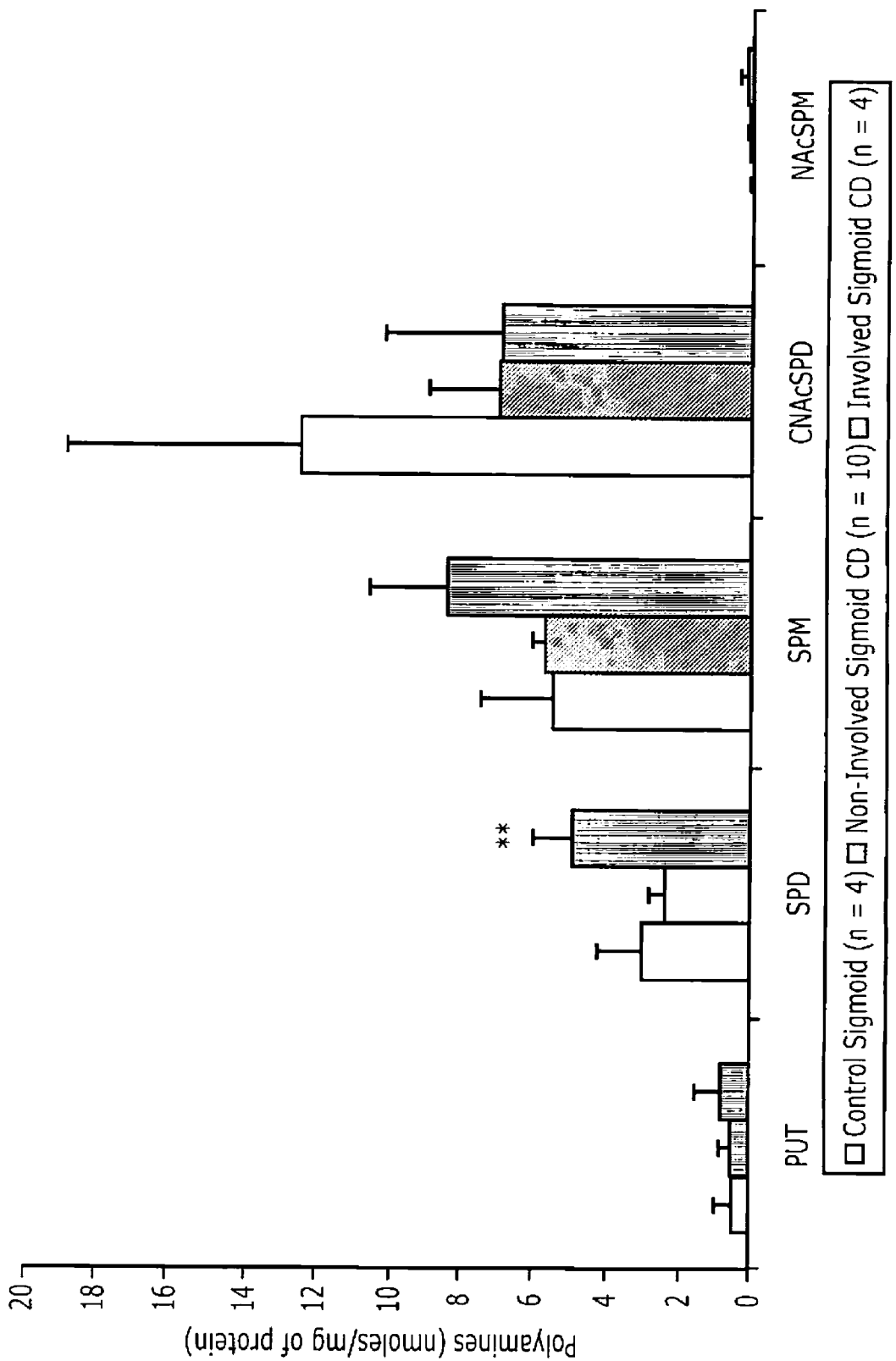
FIG. 11 depicts the effect of tissue involvement on PA levels in the sigmoid of Crohns disease subjects.
Figure 12:
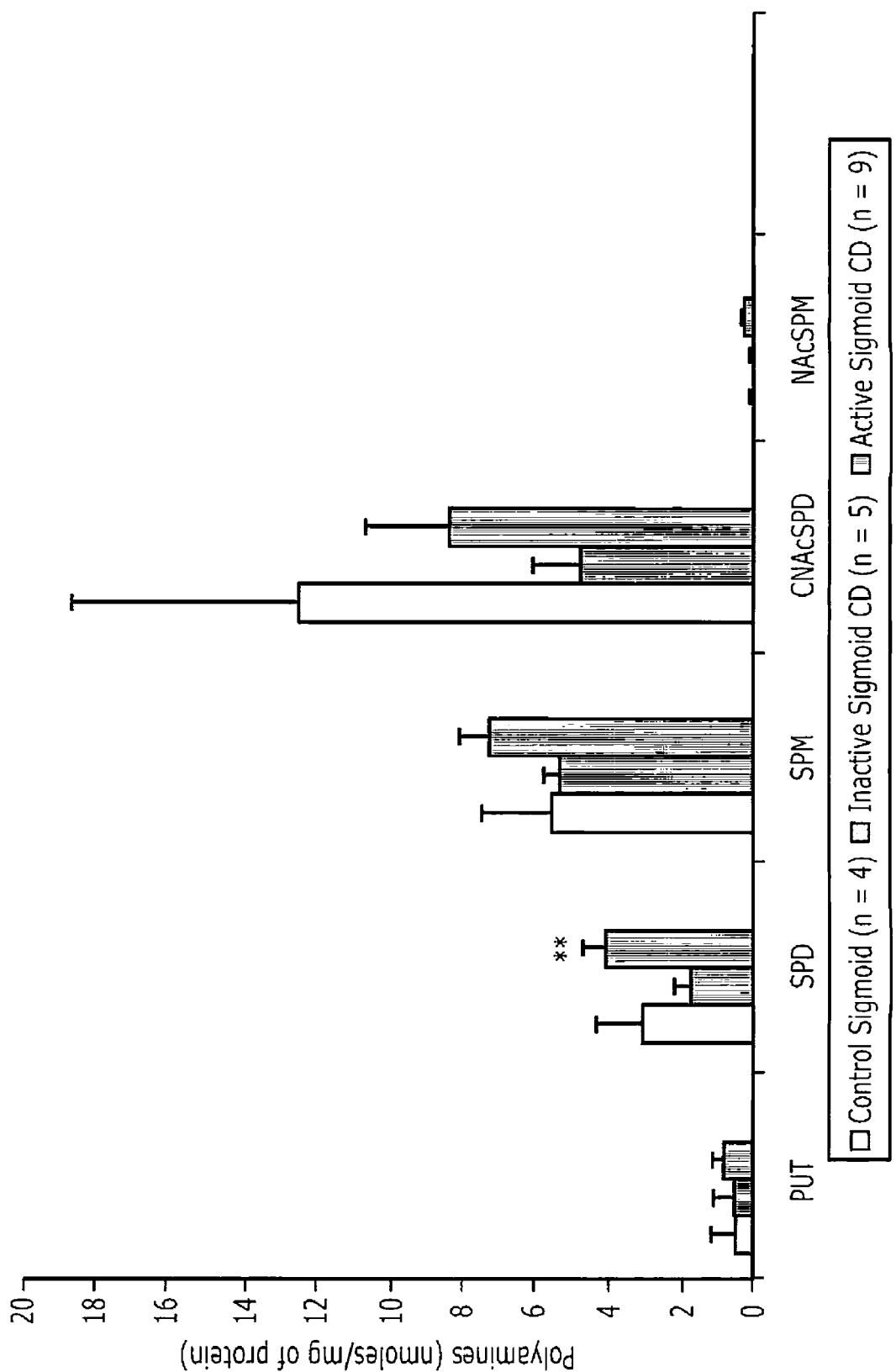
FIG. 12 Effect of active inflammation on PA levels in sigmoid tissue from CD patients.
Figure 13:
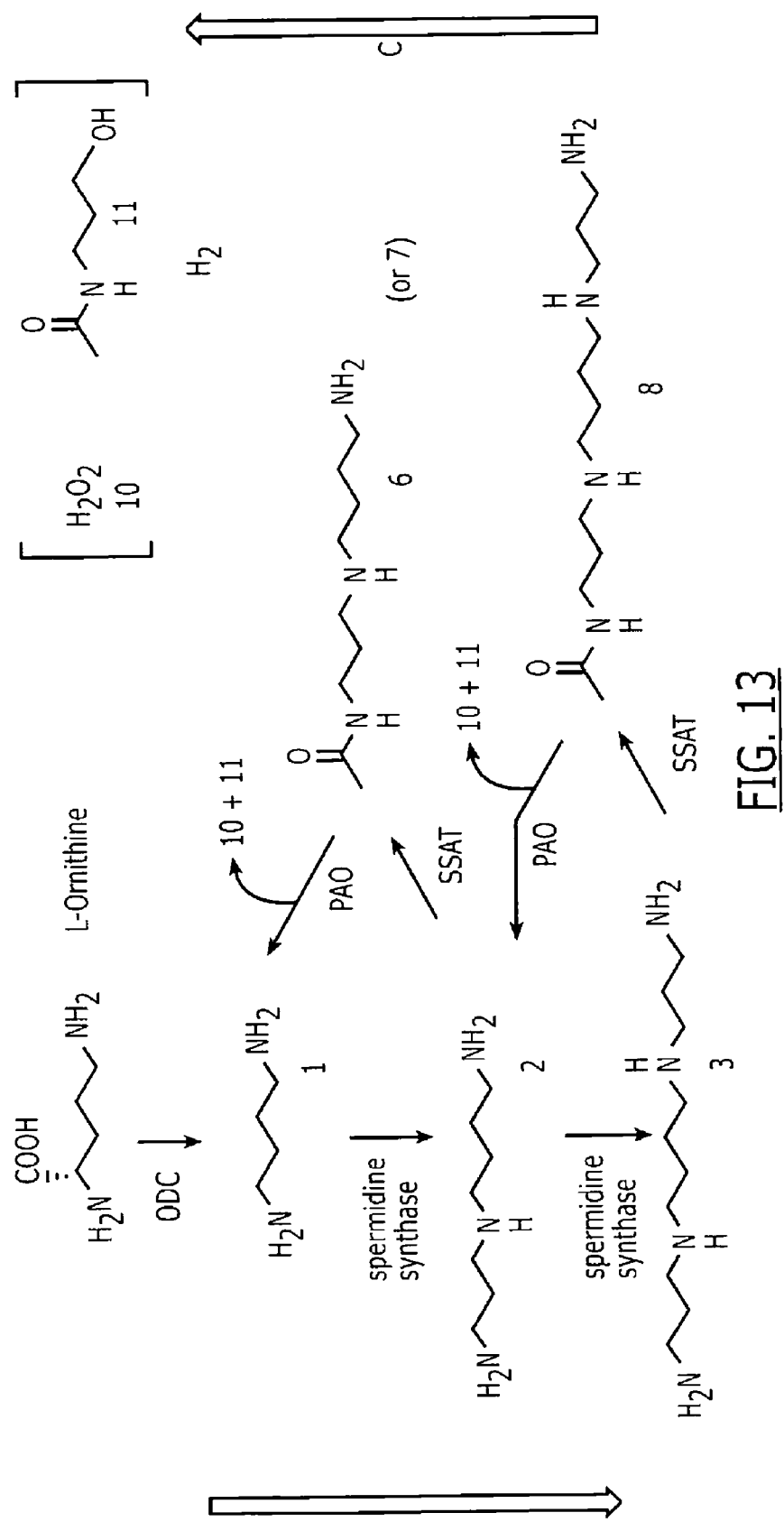
FIG. 13 shows polyamine metabolism Scheme 1.
Figure 14:
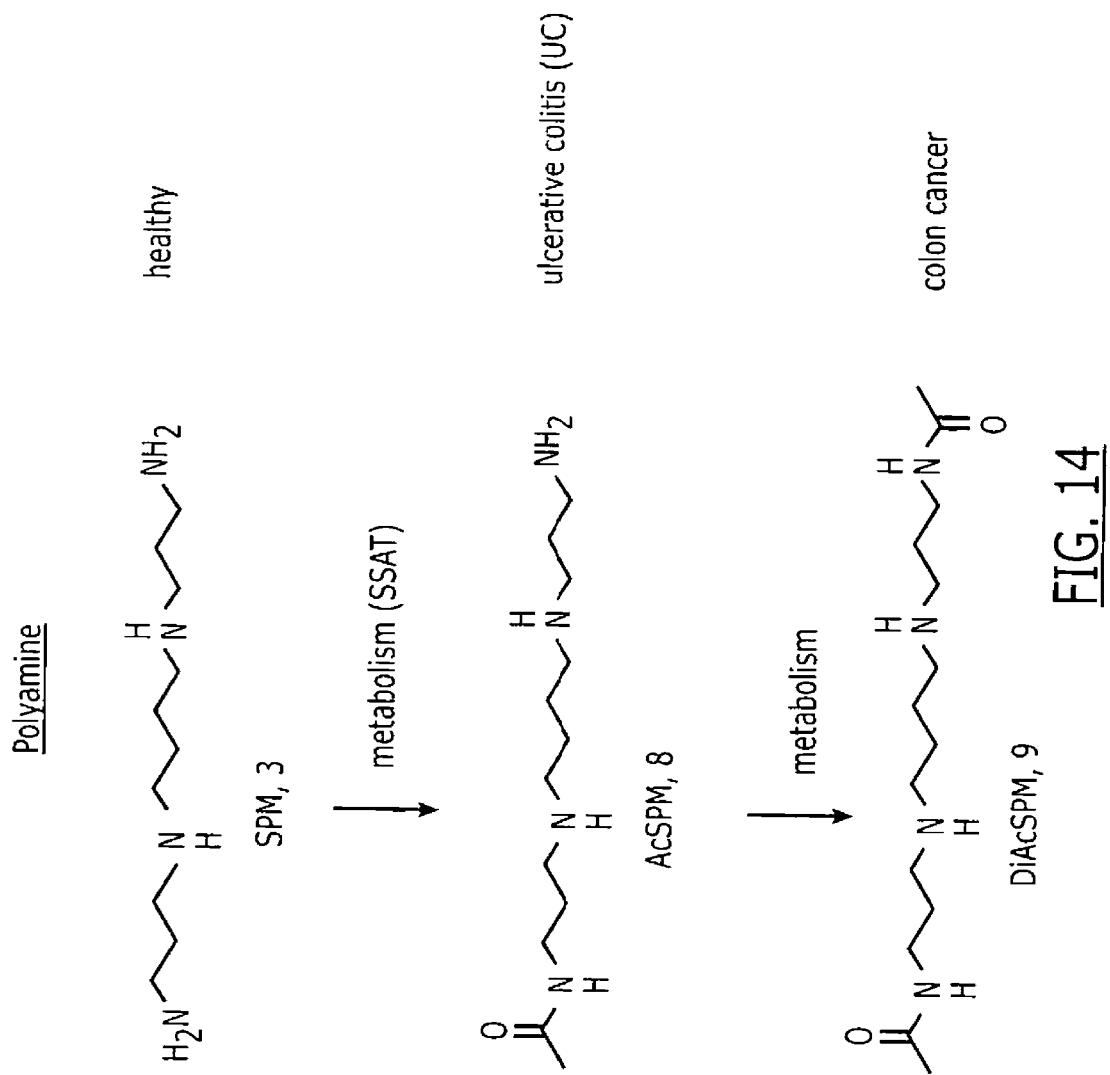
FIG. 14 illustrates polyamine metabolites and disease progression to colon cancer, according to an embodiment of the present invention.

The possibility that the polyamine metabolites themselves (8 and 9) could be diagnostic agents, which identify the conversion of ulcerative colitis tissue into colon cancer is most provocative. The fact that the di-acetylated spermine 9 is a known biomarker for colon cancer[6-9] suggests that elevated levels of its immediate precursor, the monoacetylated spermine 8, may be a potential predictor of the 'cancer transition' (FIG. 6). The fact that 8 is elevated in UC, a disease known to eventually convert to colon cancer, may be more than a remarkable coincidence. Indeed, future studies will pursue this intriguing possibility.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES 1. a) Tabor, C. W.; Tabor, H. Polyamines. *Annu. Rev. Biochem.* 1976, 45, 285; b) Pegg, A. E. *Biochem. J.* 1986, 234, 249; c) Seiler, N., Dezeure, F. Polyamine Transport in mammalian cells. *Int. J. Biochem.* 1990, 22, 211-218.
2. a) Aikens, D.; Bunce, S.; Onasch. F.; Parker, III, R.; Hurwitz, C.; Clemans, The Interactions between nucleic acids and polyamines II. Protonation Constants and $^{13}$C NMR Chemical Shift assignments of Spermidine, Spermine and Homologs. *Biophys. Chem.* 1983, 17, 67-74. b) Onasch, F.; Aikens, D.; Bunce, S.; Schwartz, H.; Nairn, D.; Hurwitz, C. The Interactions between nucleic acids and polyamines III. Microscopic Protonation Constants of Spermidine. *Biophys. Chem.* 1984, 19, 245-253.
3. Gardner, R. A.; Delcros, J.-G.; Konate, F. Breitbeil III, F.; Martin, B.; Sigman, M.; Huang, M.; Phanstiel IV, O. $N^1$-Substituent Effects in the Selective Delviery of Polyamine Conjugates into Cells Containing Active Polyamine Transporters. *J. Med. Chem.* 2004, 47, 6055-6069.
4. Seiler, N.; Delcros, J.-G.; Moulinoux, J. P. Polyamine Transport in Mammalian Cells. An Update. *Int. J. Biochem. Cell Biol.* 1996, 28, 843-861.
5. Françoise I. Bussière, Rupesh Chaturvedi, Yulan Cheng, Alain P. Gobert, Mohammad Asim, Darren R. Blumberg, Hangxiu Xu, Preston Y. Kim, Amy Hacker||, Robert A. Casero, Jr. and Keith T. Wilson, Spermine Causes Loss of Innate Immune Response to *Helicobacter pylori* by Inhibition of Inducible Nitric-oxide Synthase Translation. *J. Biol. Chem.* 2005, 280, 2409-2412.
6. Kawakita, M.; Hiramatsu, K. Diacetylated derivatives of spermine and spermidine as novel promising tumor markers. *J. Biochem.* 2006, 139, 315-322.
7. Hiramatsu, K.; Takahashi, K.; Yamaguchi, T.; Matsumoto, H.; Miyamoto, H.; Tanaka, S.; Tanaka, C.; Tamaori, Y.; Imajo, M.; Kawaguchi, M.; Toi, M.; Mori, T.; Kawakita, M. $N^1, N^{12}$ Diacetylspermine as a sensitive and specific novel marker for early and late stage colorectal and breast cancers. *Clin Cancer Res.* 2005, 11, 2986-2990.
8. Hiramatsu, K.; Sugimoto, M.; Kamei, S.; Hoshino, M.; Kinoshita, K.; Iwasaki, K.; Kawakita, M. Diagnostic and prognostic usefulness of $N^1$, $N^8$-diacetylspermidine and $N^1$, $N^{12}$-diacetylspermine in urine as novel markers of malignancy. *J. Cancer Res. Clin. Oncol.* 1997, 123, 539-545.
9. Sugimoto, M.; Hiramatsu, K.; Kamei, S.; Kinoshita, K.; Hoshino, M.; Iwasaki, K.; Kawakita, M. Significance of urinary $N^1, N^8$-diacetylspermidine and $N^1, N^{12}$-diacetylspermine as indicators of neoplastic diseases. *J. Cancer Res. Clin. Oncol.* 1995, 121, 317-319.
10. Zhang, M.; Borovikova, L. V.; Wang, H.; Metz, C.; Tracey, K. J. Spermine inhibition of monocyte activation and inflammation. *Mol. Med.* 1999, 5, No. 9, 595-605.
11. Bulychev, A. G.; Johansson, A.; Lundborg, M.; Camner, P.; Afzelius, B. A. Effects of spermidine on function and ultrastructure of aveolar macrophages. *Exp. Mol. Pathol.* 1994, 60, No. 1, 52-59.
12. a) Hugot, J. P.; Zouali, H.; Lesage, S. Lessons to be learned from the NOD2 gene in Crohn's disease. *Eur. J. Gastroenterol. Hepatol.* 2003, 15, 593-597; b) Tamboli, C. P.; Cortot, A.; Colombel, J. F. What are the major arguments in favour of the genetic susceptibility for inflammatory bowel disease? *Eur. J. Gastroenterol. Hepatol.* 2003, 15, 587-592. c) Ogura, Y.; Bonen, D. K.; Inohara. N.; Nicolae, D. L.; Chen, F. F.; Ramos, R.; Britton, H.; Moran, T.; Karaliuskas, R.; Duerr, R. H.; Achkar, J.-P.; Brant, S. R.; Bayless, T. M.; Kirschner, B. S.; Hanauer, S. B.; Nunez, G.; Cho, J. H. A frameshift mutation in NOD2 associated with susceptibility to Crohn's disease. *Nature* 2001, 411, 603-606.
13. Moncada, D. M.; Kammanadiminti, S. J.; Chadee, K. Mucin and Toll-like receptors in host defense against intestinal parasites. *Trends in Parasitol.* 2003, 19, 305-311.
14. a) Bergeron, R. J.; McManis, J. S.; Liu, C. Z.; Feng, Y.; Weimar, W. R.; Luchetta, G. R.; Wu, Q.; Ortiz-Ocasio, J.; Vinson, J. R. T.; Kramer, D.; Porter, C. Anitproliferative Proerties of Polyamine Analogues: a Structure-Activity Study. *J. Med. Chem.* 1994, 37. 3464-3476; b) Bergeron, R. J.; Feng, Y.; Weimar, W. R.; McManis, J. S.; Dimova, H.; Porter, Carl; Raisler, B.; Phanstiel, O. A Comparison of Structure-Activity Relationships between Spermidine and Spermine Analogue Antineoplastics. *J. Med. Chem.* 1997, 40, 1475-1494.
15. a) Sartor, R. B. Innate immunity in the pathogenesis and therapy of IBD. *J. Gastroenterol.* 2003, 38, 43-47.; b) Fellerman, K.; Wehkamp, J.; Herrlinger, K. R.; Stange, E. F. Crohn's disease: a defensin deficiency syndrome? *Eur. J. Gastroenterol. Hepatol.* 2003, 15, 627-634.; c) Folwaczny, C.; Glas, J; Torok, H. P. Crohn's disease: an immunodeficiency? *Eur. J. Gastroenterol. Hepatol.* 2003, 15, 621-626.; d) Cashman, K. D.; Shanahan, F. Is nutrition an aetiological factor for inflammatory bowel disease? *Eur. J. Gastroenterol. Hepatol.* 2003. 15, 607-613.; e) Rath, H. C. The role of endogenous bacterial flora: bystander or the necessary prerequisite? *Eur. J. Gastroenterol. Hepatol.* 2003, 15, 615-620.
16. Lowry. O. H.; Rosenbraugh, N. J.; Farr, A. L.; Randall, R. J.; Protein measurement with the Folin Phenol reagent. *J. Biol. Chem.* 1951, 193, 265-275.
17. Takatsuka, Y.; Yamaguchi, Y.; Ono, M.; Kamio, Y. Gene cloning and molecular characterization of lysine decarboxylase from *Selenomonas ruminantium* delineate its evolutionary relationship to ornithine decarboxylases from eukaryotes. *J. Bacterial.* 2000, 182. No. 23, 6732-6741.
18. Yamaguchi, Y.; Takatsuka, Y.; Matsufuji, S.; Murakami, Y.; Kamio, Y. Characterization of a Counterpart to mammalian Ornithine Decarboxylase Antizyme in Prokaryotes. *J. Biol. Chem.* 2006, 281, No. 7, 3995-4001.

19. Ha, H. C.; Woster, P. M.; Yager, J. D.; Casero, Jr., R. A. The role of polyamine catabolism in polyamine analogue-induced programmed cell death. *Proc Natl Acad Sci USA*. 1997, 94, 11557-11562.
20. Peulen, O.; Deloyer, P.; Deville, C.; Dandrifosse, G. Polyamines in Gut Inflammation and Allergy. *Curr. Med. Chem.—Anti-Inflammatory& Allergy Agents* 2004, 3, 1-8.
21. Obayashi, M.; Matsui-Yuasa, I.; Matsumoto, T.; Kitano, A.; Kobayashi, K.; Otani, S. Polyamine metabolism in colonic mucosa from patients with ulcerative colitis. *Am. J. Gastroenterol.* 1992, 87, 736-740.
22. Weiss, T. S.; Herfarth, H.; Obermeier, F.; Ouart, J.; Vogl, D.; Schölmerich, J.; Jauch, K.-W.; Rogler, G. Intracellular Polyamine Levels of Intestinal Epithelial Cells in Inflammatory Bowel Disease. *Inflamm. Bowel Dis.* 2004, 10, 529-535.
23. Naser, S., unpublished results.
24. Covassin. L.; Desjardins, M.; Charest-Gaudreault, R.; Audette, M.; Bonneau, M. J.; Poulin, R. Synthesis of spermidine and norspermidine dimers as high affinity polyamine transport inhibitors. *Bioorg. Med. Chem. Lett.* 1999, 9, 1709-1714.
25. Estebe, J.-P.; François, Legay; Gentili, M.; Wodey, E.; Leduc, C.; Ecoffey, C.; Moulinoux, J.-P. Evaluation of a Polyamine-Deficient Diet for the Treatment of Inflammatory Pain. *Anesth. Analg.* 2006, 102, 1781-1788.

That which is claimed:

1. A diagnostic test indicative of inflammatory bowel disease (IBD) in a human patient, the test comprising:
    obtaining a sample of mucosal tissue from the ileum or sigmoid colon of the patient;
    evaluating sample quality by testing for cadaverine and continuing the diagnostic test if the sample has no detectable cadaverine;
    testing the cadaverine negative sample for N-acetylated spermine; and
    correlating a higher than normal level of N-acetylated spermine in the sample with presence of IBD in the patient.

2. A diagnostic test indicative of inflammatory bowel disease (IBD) in a symptomatic patient having an intestinal mucosa which appears normal by endoscopy, the test comprising:
    obtaining a sample of mucosal tissue from the ileum or sigmoid colon of the patient;
    determining the sample has no detectable cadaverine before further testing;
    testing the cadaverine negative sample for spermidine, spermine and N1-acetylated spermine;
    comparing test results of the sample to values for ileal or sigmoid mucosal tissue from normal subjects; and
    correlating a higher than normal level of spermine, spermidine and N-acetylated spermine as indicative of inflammatory bowel disease in the patient.

3. A diagnostic test indicative of inflammatory bowel disease in a patient having clinical symptoms consistent with said disease, the test comprising:
    obtaining a sample of intestinal mucosa from the patient;
    ascertaining the sample tests negative for cadaverine;
    testing the cadaverine negative sample for spermidine;
    comparing the sample's spermidine level to level of spermidine in normal intestinal mucosal tissue; and
    correlating a higher than normal level of spermidine as indicative of inflammatory bowel disease in the patient.

4. A diagnostic test for an inflammatory bowel disease in a patient symptomatic therefor, the test comprising:
    isolating mononuclear leukocytes from the patient's blood;
    testing the isolated mononuclear leukocytes for level of spermidine; and
    correlating a level of spermidine higher than that in mononuclear leukocytes of normal subjects as indicative of an inflammatory bowel disease in the patient.

5. A diagnostic test indicative of ulcerative colitis in a patient symptomatic for an inflammatory bowel disease, the test comprising:
    obtaining a sample of intestinal mucosa from the patient;
    ascertaining the sample tests negative for cadaverine;
    testing the cadaverine negative sample for levels of spermidine and N-acetylated spermine;
    comparing the sample's levels of spermidine and N-acetylated spermine to those in intestinal mucosa from normal subjects; and
    correlating higher than normal levels of spermidine and N-acetylated spermine as indicative of ulcerative colitis in the patient.

* * * * *